United States Patent [19]

Hsieh et al.

[11] Patent Number: 5,145,567
[45] Date of Patent: Sep. 8, 1992

[54] CAPILLARY ZONE ELECTROPHORETIC ANALYSIS OF ISOENZYMES

[75] Inventors: You-Zung Hsieh, Taipei, Taiwan; Fu-Tai A. Chen, Brea, Calif.; James C. Sternberg, Fullerton, Calif.; Gerald Klein, Orange, Calif.; Cheng-Ming Liu, Yorba Linda, Calif.

[73] Assignee: Beckman Instruments, Inc., Fullerton, Calif.

[21] Appl. No.: 792,313

[22] Filed: Nov. 14, 1991

[51] Int. Cl.⁵ .................. G01N 27/26; B01D 57/02
[52] U.S. Cl. ....................... 204/180.1; 204/299 R
[58] Field of Search ...................... 204/180.1, 299 R

[56] References Cited

U.S. PATENT DOCUMENTS

| | | | |
|---|---|---|---|
| 4,254,084 | 3/1981 | Blum | 204/182.8 X |
| 4,259,079 | 3/1981 | Blum | 204/182.3 |
| 4,459,198 | 7/1984 | Mizuno et al. | 204/299 R |
| 4,909,919 | 3/1990 | Morris et al. | 204/299 R |

OTHER PUBLICATIONS

A. Kopwillem, "Analytical isotachophoresis in capillary tubes, Transformation of pyruvate to succinate by calf heart mitochondrial enzymes" Journal of Chromatography, 82(1973) 407-409.

Stellan Hjertén and Ming-De Zhu, "Micropreparative Version of High-Performance Electrophoresis: The Electrophoretic Counterpart of Narrow-Bore High-Performance Liquid Chromatography" Journal of Chromatography 327(1985) 157-164.

Peter Stehle, Hans-Peter Bahsitta & Peter Fürst, "Analytical Control of Enzyme-Catalyzed Peptide Synthesis Using Capillary Isotachophoresis" Journal of Chromatography 370(1986) 131-138.

Beckman Product Bulletin 6234, "The Appraise ® and Paragon ® Electrophoresis System".

Primary Examiner—John Niebling
Assistant Examiner—John S. Starsiak
Attorney, Agent, or Firm—William H. May; Arnold Grant; Richard P. Burgoon, Jr.

[57] ABSTRACT

Disclosed herein is a methodology for analyzing isoenzymes using capillary zone electrophoresis ("CZE") techniques. Briefly, an isoenzyme-containing sample and a substrate capable of being catalyzed by said isoenzyme into a reaction product are introduced into a capillary column comprising a buffer. Most preferably, the buffer contains the substrate prior to introduction of the sample into such substrate-buffer. CZE separation techniques are applied to the column such that the isoenzymes are separated from each other into discrete zones. The separation techniques are terminated such that product is rapidly generated by the catalytic conversion of substrate by the isoenzymes, and accumulated, within each discrete zone, followed by detection of product. Information regarding the relative distribution of the isoenzymes can be derived from the relative distribution of the product.

10 Claims, 7 Drawing Sheets

CAPILLARY ZONE ELECTROPHORETIC ANALYSIS OF ISOENZYMES

FIELD OF THE INVENTION

The present invention is directed to the analysis of samples in general, the analysis of samples by capillary zone electrophoresis in particular, and specifically the analysis of isoenzymes by capillary zone electrophoresis. In a particularly preferred embodiment, the invention is directed to the analysis of clinical isoenzymes by capillary zone electrophoresis.

BACKGROUND OF THE INVENTION

Enzymes are proteins having catalytic properties. A "catalyst" increases the rate of a particular chemical reaction without itself being consumed or permanently altered; at the end of a catalyzed reaction, the main reaction products have undergone transformation into new products, but the catalyst appears unchanged in form and quantity. Thus the presence of a small number of enzyme molecules in a reaction mixture involving a substrate can convert a greater number of the substrate molecules to products. Similarly, an increase in the amount of an enzyme in a sample, such as, for example, a clinical sample (e.g., serum, plasma, cerebro spinal fluid, urine), can be detected with great specificity because of the unique and characteristic effect that the enzyme has on the chemical reaction which it catalyzes.

Isoenzymes are two or more enzymes which catalyze the same (or similar) specific reactions but which have different physical properties, e.g., electrophoretic mobility, resistance to chemical or thermal inactivation, etc. Thus, while in a class of isoenzymes, each will have the same catalytic function, subtle, yet detectable differences between each can be determined such that, in a sample material, the relative distribution of each isoenzyme having the same catalytic function can be determined.

Analysis of the presence of enzymes from clinical samples is diagnostically valuable. Specific enzymes are associated with specific tissue sources. For example, the enzyme lactate dehydrogenase ("LDH") is found principally in the heart, liver, skeletal muscle and lymph nodes. Creatine kinase ("CK") is found principally in skeletal muscle, brain, heart and smooth muscle. Cholinesterase ("CHE") is found principally in the liver. When these tissue sources are damaged (due to internal causes, such as disease, or external sources, such as alcohol), there is typically a release of the enzyme(s) associated therewith into the blood stream. Accordingly, a clinical sample can be analyzed and if elevated levels of, for example, LDH, are identified, possible damage to the associated tissues is evident.

LDH has five isoenzymes. It is well known that certain diseases will cause a change in the relative distribution of LDH isoenzymes occurring in serum. LDH is a hydrogen transfer enzyme that catalyzes the oxidation of L-lactate to pyruvate with the mediation of nicotinamide adenine dinucleotide (NAD+) as the hydrogen acceptor. Thus, in the presence of LDH, L-lactate and NAD+ will be catalytically converted to pyruvate and NADH. NADH production can be measured and the amount can be correlated with the amount of LDH in the sample. Each LDH isoenzyme has a unique concentration in a given sample. Similarly each isoenzyme is capable of catalyzing the L-lactate/NAD+ reaction. Thus each isoenzyme will produce different amounts of NADH by such catalysis.

Electrophoretic separation on agarose gels or cellulose acetate is a well known procedure used to demonstrate the presence of LDH isoenzymes in a sample. Typically, a clinical sample (e.g. serum) is inserted into a well in the gel surface and a voltage impressed across the gel. Since each isoenzyme has a unique electrophoretic mobility, the voltage separates the isoenzymes from each other. A reaction mixture is then layered over the separation medium and, following sufficient incubation, the NADH generated over the individual LDH zones is detected (typically by fluorescence when the NADH is excited by ultraviolet light). Thereafter, the gel patterns may be read directly by observing the relative intensities of the bands, or scanned by, e.g., color densitometer instruments, such that relative peak distribution can be obtained. Such an electrophoresis system is commercially available from Beckman Instruments, Inc. (Fullerton, Calif., USA) under the trademarks APPRAISE ® and PARAGON ®.

Many clinically significant isoenzyme product patterns have been correlated with certain disease states. Again focusing on LDH, a normal LDH distribution pattern will evidence a "darker" band (or higher peak) for LDH-2 vis-a-vis LDH-1, whereas a serum sample obtained from an individual having acute myocardial infarction will evidence a darker (or higher) LDH-1 band vis-a-vis LDH-2, the so-called "flipped" LDH-1.

As noted, isoenzymes have different physical properties, e.g., different electrophoretic mobilities. Accordingly, isoenzymes lend themselves to analysis by capillary zone electrophoresis ("CZE"). CZE is a technique which permits rapid and efficient separations of charged substances. In general, CZE involves introduction of a sample into a capillary tube, i.e., a tube having an internal diameter from about 5 to about 2000 microns, and the application of an electric field to the tube. The electric potential of the field both pulls the sample through the tube and separates it into its constituent parts. Each constituent of the sample has its own individual electrophoretic mobility; those having greater mobility travel through the capillary tube faster than those with slower mobility. As a result, the constituents of the sample are resolved into discrete zones in the capillary tube during their migration through the tube. An on-line detector can be used to continuously monitor the separation and provide data as to the various constituents based upon the discrete zones.

CZE can be generally separated into two categories based upon the contents of the capillary columns. In "gel" CZE, the capillary tube is filled with a suitable gel, e.g., polyacrylamide gel. Separation of the constituents in the sample is predicated in part by the size and charge of the constituents travelling through the gel matrix. In "open" CZE, the capillary tube is filled with an electrically conductive buffer solution. Upon ionization of the capillary, the negatively charged capillary wall will attract a layer of positive ions from the buffer. As these ions flow towards the cathode, under the influence of the electrical potential, the bulk solution (the buffer solution and the sample being analyzed), must also flow in this direction to maintain electroneutrality. This electroendosmatic flow provides a fixed velocity component which drives both neutral species and ionic species, regardless of charge, towards the cathode. Fused silica is principally utilized as the material for the capillary tube because it can withstand the relatively high voltage used in CZE, and because the inner walls of a fused silica capillary ionize to create the negative charge which causes the desired electroendosomatic flow.

The inner wall of the capillaries used in CZE can be either coated or uncoated. The coatings used are varied and known to those in the art. Generally, such coatings are utilized in order to reduce adsorption of the charged constituent species to the charged inner wall. Similarly, uncoated columns can be used. In order to prevent such adsorption, the pH of the running buffer, or the components within the buffer, are manipulated.

While the different electrophoretic mobilities of isoenzymes suggests the applicability of CZE analytical techniques, a practical problem exists as to the parameters of such testing. This is because in order to determine the presence of isoenzymes in a sample, it is necessary to rely upon their catalytic activity relative to a substrate. Thus, in the electrophoresis system described above, separation of the isoenzymes must take place before addition of the substrate. However, this is not possible with CZE because there is presently no practical way to "add" the substrate to the sample after the constituent parts thereof have been separated.

What is needed, then, is a method for analyzing isoenzymes that exploits the speed and accuracy of CZE techniques.

SUMMARY OF THE INVENTION

The present invention satisfies at least the above need by providing a capillary zone electrophoresis method for the analysis of isoenzyme constituents to be separated comprising the steps of:

a) introducing an isoenzyme-containing sample and a substrate capable of being catalyzed to a reaction product by said isoenzymes into a capillary tube containing therein a buffer;

b) subjecting said sample to capillary zone electrophoresis techniques by applying an electric field to said capillary tube of sufficient voltage to allow for the separation of said sample into its isoenzyme constituent parts;

c) terminating the application of said electric field;

d) allowing a sufficient period of time to transpire to permit said isoenzymes to catalytically convert said substrate to a reaction product;

e) moving said reaction product through said tube to a detection region; and f) detecting said reaction product.

Most preferably, the substrate is included within the buffer prior to introduction of the sample into the capillary tube. In accordance with the present in invention, the isoenzymes in the sample are separated from each other using CZE techniques, followed by termination of the electric field. This separates the isoenzymes in the sample into discrete zones within the buffer. As such, product formation arising from the catalytic conversion of the substrate by the isoenzymes will take place within these discrete zones. Application of an electric field following this period allows these product zones to continue moving through the capillary to a detection region, where the product zones are resolved by, e.g., peaks of various widths and height. By analyzing such peaks, a clinician can determine the relative distribution of each isoenzyme within the sample such that clinical evaluations can be obtained.

DETAILED DESCRIPTION OF PREFERRED EMBODIMENTS

Typically, extremely small quantities of an enzyme are all that is needed to catalyze a Substrate (S)→Product (P) reaction. Thus, while an enzyme itself may not be detectable (due to the small quantities typically present in a sample), the amount of reaction product catalyzed by the enzyme can be detected and used as an indicator of the relative amount of enzyme present in the sample. The catalytic activity of an enzyme, in the presence of substrate, is nearly instantaneous. Accordingly, product will be created rapidly until either the reaction is terminated, substrate depletion occurs (i.e. all of the substrate is converted to product) or the reaction is reversed (i.e. product is converted to substrate by manipulation of, e.g., the reaction medium pH, temperature or conditions). In order to effectively measure the presence of specific isoenzymes in a sample based upon the conversion of substrate into reaction product, it is necessary to separate the isoenzymes from each other before addition of substrate. State again, heretofore if substrate and isoenzymes were co-mingled before separation of the isoenzymes, product would be rapidly produced, thus making the desired "separation" unattainable.

Applicants have discovered, however, that the isoenzyme-containing sample and a buffer-containing substrate can be co-mingled "prior" to separation via CZE techniques by utilization of the present methodology. The present methodology is initiated by introducing an isoenzyme-containing sample and a substrate capable of being catalytically converted to a reaction product by said isoenzymes into a capillary column comprising a buffer. Most preferably, the substrate is included within the buffer ab initio. Sample introduction can be accomplished by, e.g., the electrokinetic injection method (i.e., where a short application of an electric field is applied to the column such that a sample "plug" is drawn into the capillary column) or by pressure injection (i.e., where pressure is used to "drive" a sample plug into the capillary column). Those skilled in the art will fully understand these two injection approaches; either may be used with the present invention. Reference is now made to FIG. 1 for elucidation of the methodology.

Figure 1A:
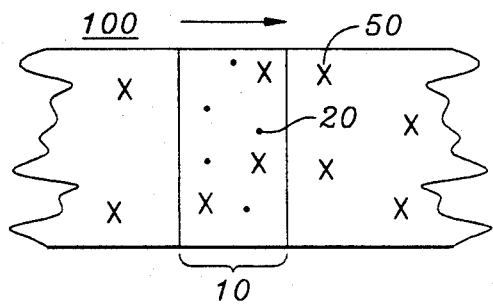
FIG. 1A is a depiction showing the initial entry of the sample comprising isoenzymes into the capillary tube comprising substrate buffer.

FIG. 1A represents the post-sample-plug introduction into the capillary column. The sample-plug 10 is pulled into the column 100, where it co-mingles with the buffer comprising substrate 50; this leads to the catalytic conversion of substrate into product 20 within the region of the plug.

Figure 1B:
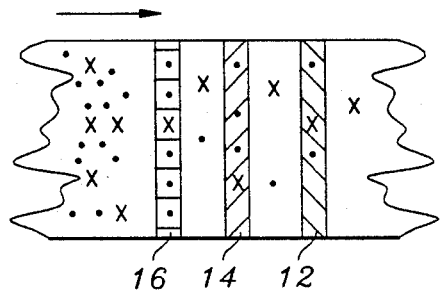
FIG. 1B is a further depiction of the sample of FIG. 1A separated into isoenzyme constituent parts.

Following introduction of the plug into the capillary, the isoenzyme constituents are separated based upon their individual electrophoretic mobilities. This is represented in FIG. 1B where three isoenzymes zones, 12, 14 and 16, are separated from one another. Within each zone, some product will be formed during the traverse of the zones through the column; to the extent that the isoenzymes have a faster (relative) electrophoretic mobility than the product originally formed during initial sample introduction, then such original product will, in effect, proceed behind the isoenzymes.

As those skilled in the art appreciate, one can achieve faster speeds through a capillary by increasing the voltage applied thereto, and vice-versa. In the presently disclosed protocol, however, a period of time is required where the sample is not traversing the column. During this so-called "park" period, reaction product is rapidly accumulated within the separated zones. Thus, the application of the electric field to the column, and the time of such application, cannot be such that the separated sample constituents will reach the detection area of the CZE instrument prior to the required "park" period. By increasing or decreasing the voltage applied to the column, the time of sample transition can be adjusted such that the park period can be initiated prior to a point where sample has reached the detection region of the instrument. Most preferably, the park period begins when the sample is approximately half-way through the column, although this is not critical. What is critical is that the park period must begin before any isoenzyme sample has reached the detection region.

Figure 1C:
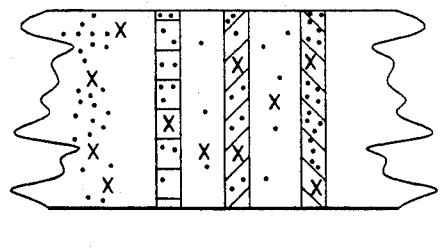
FIG. 1C is a further depiction of the sample of FIG. 1A where the analysis is in the "park" mode.

Reference is now made to FIG. 1C, which illustrates the park period. During this period, the applied voltage is terminated—this has the effect of substantially stopping the flow of all materials through the capillary column. I.e., each separated isoenzyme is "parked" in a specified zone. This, then, allows for the catalytic conversion of substrate into product within these discrete zones. During the park period, product is rapidly produced and accumulated within these zones.

Another factor which is of import to the park period is the time for parking. The amount of time for parking is dependent upon the amount of detectable reaction product likely to be produced within the discrete isoenzyme zones. This is a function of at least two factors, the amount of substrate available, and the physiological amount of the enzyme available.

The park time is limited principally by the amount of substrate present in the buffer via the affects of substrate depletion. I.e., if the park time is too long and there is insufficient amount of substrate in the buffer, the Substrate→Product reaction will terminate. Accordingly, there should be sufficient substrate within the buffer to prevent substrate depletion. This can be avoided by adding at least twice the $K_m$ value for a given substrate to the buffer, where $K_m$ is equal to the substrate concentration at which the initial reaction rate is half maximal. Such $K_m$ values can be determined using the techniques described in, for example, *Biochemistry*, 2nd Ed. Chpt. 8, p. 193, Lehninger, Ed. (Worth Publishers, Inc. 1975). Preferably, at least three times $K_m$ is used, and most preferably at least five times $K_m$. For example, the $K_m$ for lactate is about 10.0 mM in an LDH enzyme system; most preferably, then, the concentration of lactate in the buffer is about 50.0 mM.

Detectable product is of import because it is necessary to have a product-signal to noise (or "background") ratio of greater than at least about 2:1, preferably greater than about 50:1 and most preferable greater than about 300:1. While background noise varies typically from instrument to instrument, a level of about 100 μA is achievable and acceptable. The signal is also predicated, in part, by the unit activity of the enzyme. The unit activity of the enzyme (designated herein as "U"), is a relative value given to the enzyme based upon specific operating conditions. For example, at 25° C., pH 7.2, the unit activity for the NADH→NAD+ conversion in an LDH enzyme reaction is 1.0; at, 25° C., pH 8.7, the unit activity of NAD+→NADH conversion is approximately 0.1. Specific unit activity values for various enzymes is typically determined by the vendor and printed on the label. As such, these values are considered to be within the purview of the skilled artisan.

In order to determine a minimum park time period, the following transformant can be utilized (throughout this disclosure, the symbol "•" represent a multiplication symbol):

$$t_{min} = \frac{\frac{A}{KL}}{U \cdot IU \cdot MWp \cdot \frac{T_1}{T}} \qquad [1]$$

where:
A is the desired absorbance value of the product;
K is the molar extinction coefficient of the product; e.g., the absorbance value of 1.0M of product across a 1.0 cm path length at the maximum absorbance wavelength of the product;
L is the measuring path length through the capillary (e.g., the internal diameter of the capillary tube);
U is the unit activity value of the enzyme, at temperature T under specified conditions;
IU is a constant, $10^{-6}$/min, the enzyme activity necessary to convert one micromole of substrate to product, per minute, at temperature T;
MWp is the molecular weight of the product;
$T_1$ is the running temperature of the system; and
T is the enzyme calibration temperature.

Typically, T is equal to 25° C. The molar extinction coefficient of particular species are readily determined and are considered to be within the purview of the skilled artisan.

The catalytic activity of enzymes are typically affected by a variety of factors, e.g., temperature and pH. For example, by increasing the temperature of the reaction mixture, the kinetics of the catalytic reaction will increase, and by lowering the temperature, the kinetics decrease. For the majority of enzymes, such kinetics will increase up to about 47° C., at which point such temperatures have a deleterious affect upon, inter alia, the enzyme. Generally, adjusting the pH of the reaction mixture can drive the catalytic reaction either forward (S→P) or backwards (P→S). Accordingly, it should be readily apparent that notwithstanding the transformant of Equation 1, the minimum park time can be decreased by, e.g., increasing the running temperature, $T_1$. This is of import in analytical settings where the time of analysis is a consideration.

Figure 1D:
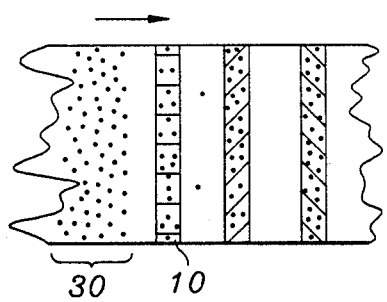
FIG. 1D is a further depiction of the sample of FIG. 1A where the movement of the product through the capillary is continuing.

Referring to FIG. 1D, after the park period, voltage is again applied to the capillary column sufficient to move the product through the column to the detection region. Alternatively, external pressure (i.e., as in the pressure-injection protocol), can be applied to the column to effectuate the same results. As noted, once the substrate and the enzyme interact (e.g., upon injection of the sample into the capillary), product will be formed. Thus, there will be a region of product, typically behind the separated isoenzyme zones, which will be detected. This region, depicted as 30 in FIG. 1D, is referred to herein as a "sample shock". The sample shock is generally comprised of the majority of product formation throughout the analysis but is not attributed to the discrete isoenzyme zones; it is attributed to the non-separated isoenzymes in toto. This region is typically segregated visually upon review of the resulting electropherogram due to the higher (relative) peak attributed thereto vis-a-vis the product peaks resulting from the isoenzymes.

EXAMPLES

The following examples directed to preferred embodiments of the invention disclosed herein are not intended, nor should they be construed, as limiting the disclosure, or the claims to follow:

I. MATERIALS AND METHODS

A. Capillary Electrophoresis Procedures

Capillary electrophoresis of samples was performed on a Beckman Instruments, Inc. high performance capillary electrophoresis system (Beckman Instruments, Inc., Fullerton, Calif., U.S.A., Model No. 357575). Data analysis was performed on System Gold ™ software (Beckman Instruments, Inc.). The aforementioned capillary electrophoresis system contains built-in 200, 206, 214, 280 and 340 nm narrow-band filters for on-line detection and quantification. Electrophoresis was performed in uncoated fused silica tubes having 75 μm i.d. and 25 cm long (Polymicro Technologies, Phoenix, Ariz. Product No. TSPO 75375). Prior to analysis, the column was filled with Substrate Buffer. The detection window is located approximately 6.5 cm from the column outlet.

LDH Isoenzyme Samples were placed on the inlet tray and introduced into the capillary by the electrokinetic method by applying 3 kV to the column for about 1 second. Isoenzymes were separated using a column voltage gradient of about 300 volts/cm for about 2 minutes. After the park period, the product was moved to the detection window using a voltage gradient of about 300 volts/cm.

For the Examples, the resulting product, NADH, was detected at 340 nm. Analysis was conducted at ambient temperature (25° C.).

B. Substrate Buffer

All chemicals were at least of ACS grade. As noted, it is most preferred that the substrate be included within the buffer and that such substrate buffer be within the capillary column prior to the introduction of sample to the column.

The Substrate Buffer utilized was Beckman DriStat ® LD-L Reagent (Beckman Instruments, Inc., part no. 270230132-A) which was diluted 1 part reagent to 4 parts distilled water. To 80 ml of the diluted reagent was added 329 mg NAD+ and 278 μl of Lactic Acid, which are substrates for the LDH isoenzymes. The pH of the Substrate Buffer was adjusted to 8.7 by drop-wise addition of 1N NaOH.

C. LDH Isoenzyme Samples

The LDH Isoenzyme Samples comprised trishydroxymethyl amino methane buffer, pH 8.4, to which was added 1.0 IU/ml each of the five purified human LDH isoenzymes, designated herein as LD-1, LD-2, LD-3, LD-4 and LD-5 (Sigma Chemical Co., St. Louis, Mo., part nos. L-3632; L-3757; L-3882; and L-6508 for LD-1; LD-2; LD-3; and LD-5, respectively; Aalto-Scientific Ltd., San Diego, Calif., part no. LD-4, P for LD-4), and 10.0 IU/ml each of LD-1 and LD-5 purified bovine isoenzymes (Boehringer Mannheim, GmbH, Germany, part nos. 106 984 and 106 992, respectively).

II. EXAMPLES

Example I-Park Period Minimum

To evaluate minimum park periods, an analysis was conducted using the bovine LD-1 and LD-5 isoenzymes (hereinafter BLD-1 and BLD-5, respectfully). Under the experimental conditions described herein, the enzyme has approximately one-tenth of the unit activity in the S→P direction (for the specified bovine LD, the desired direction of the system is P→S, and in this direction, the unit value is 10). Accordingly, the value for U is 1. A desired absorbance value for the aforementioned system is between about 0.002 and about 0.006 Absorbance Units; for this Example, a desired value for A was 0.005. The molecular weight of NADH is 665.4, and the molar extinction coefficient for NADH is 6300. The measuring path length for the aforementioned system was 0.0075 cm. Thus, a predicted minimum park time is calculated as follows (for ease of presentation, unit values are not included):

$$t_{min} = \frac{\frac{.005}{6300 \cdot 0.0075}}{1 \cdot 10^{-6} \cdot 665.4 \cdot 1}$$
$$= 1.59 \text{ min.}$$

Thus, a predicted minimum park time necessary to achieve a definitive signal to noise ratio for this system is about 90 sec. Reference is now made to FIGS. 2-5.

Figure 2:
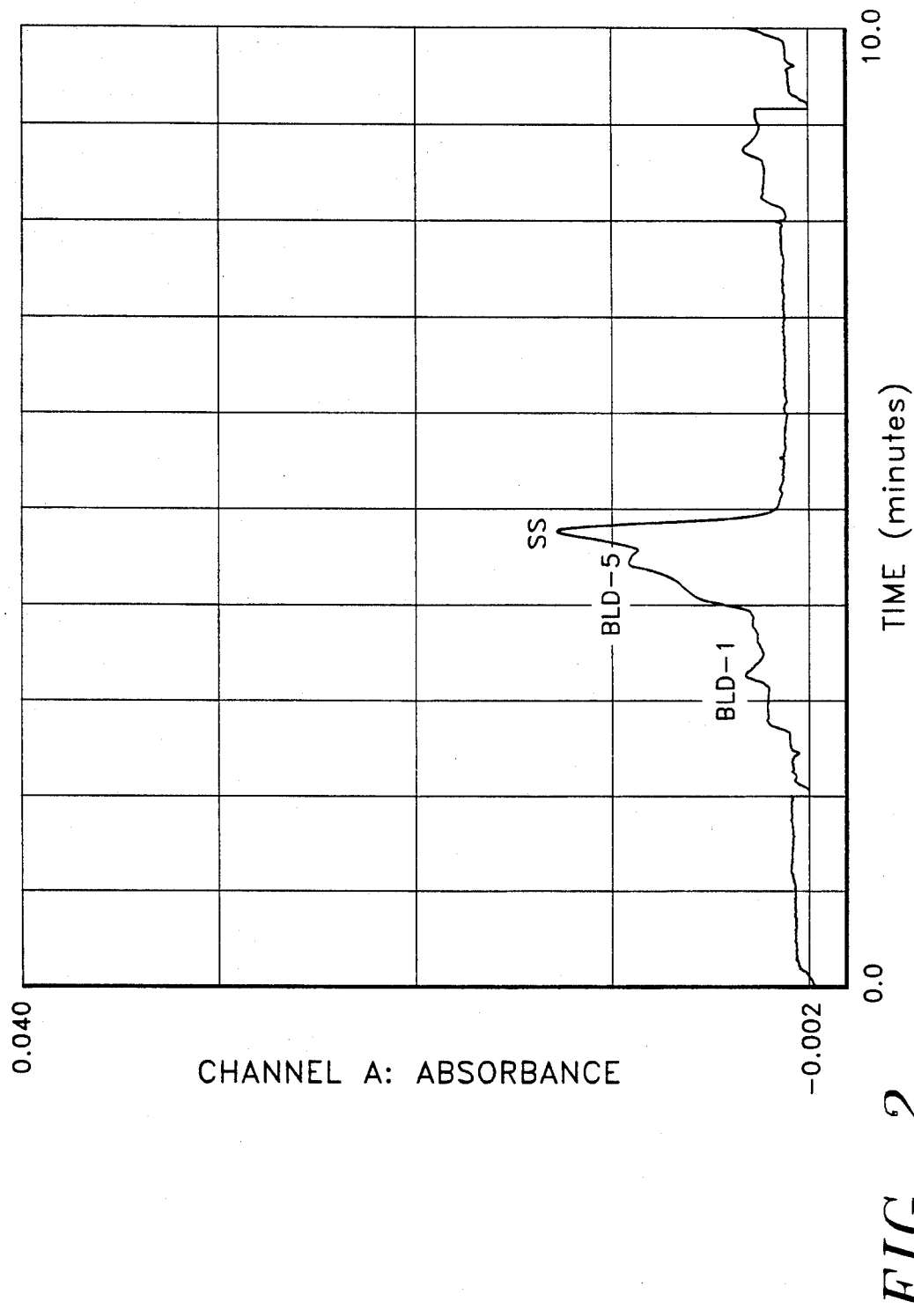
FIG. 2 is an electropherogram of NADH produced by the catalytic conversion of NAD+ and lactic acid by bovine LD-1 and LD-5 with a park time of 0 seconds.
Figure 3:
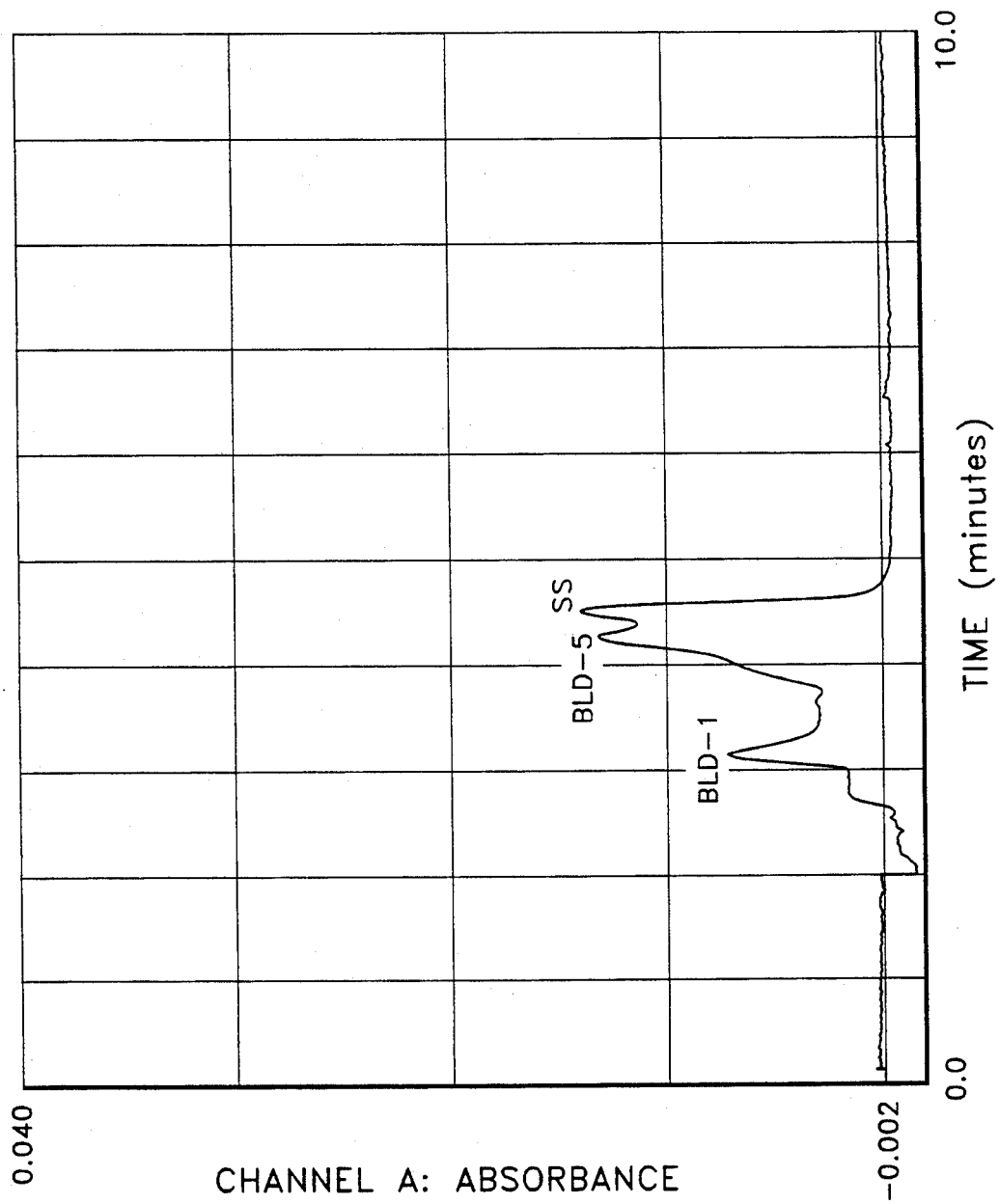
FIG. 3 is an electropherogram of the same materials of FIG. 2 with a park time of 60 seconds.

The electropherogram of FIG. 2 was generated with a 0 second park time, i.e., the analysis continued uninterrupted from introduction of the sample through detection. As is apparent, the resolution between the peaks and the sample shock ("SS") is less than ideal, as would be expected under these conditions. In FIG. 3, a park period of 60 seconds was utilized, 33% less than the predicted minimum. While the resolution is an improvement over that of the no-park condition, it is not ideal.

Figure 4:
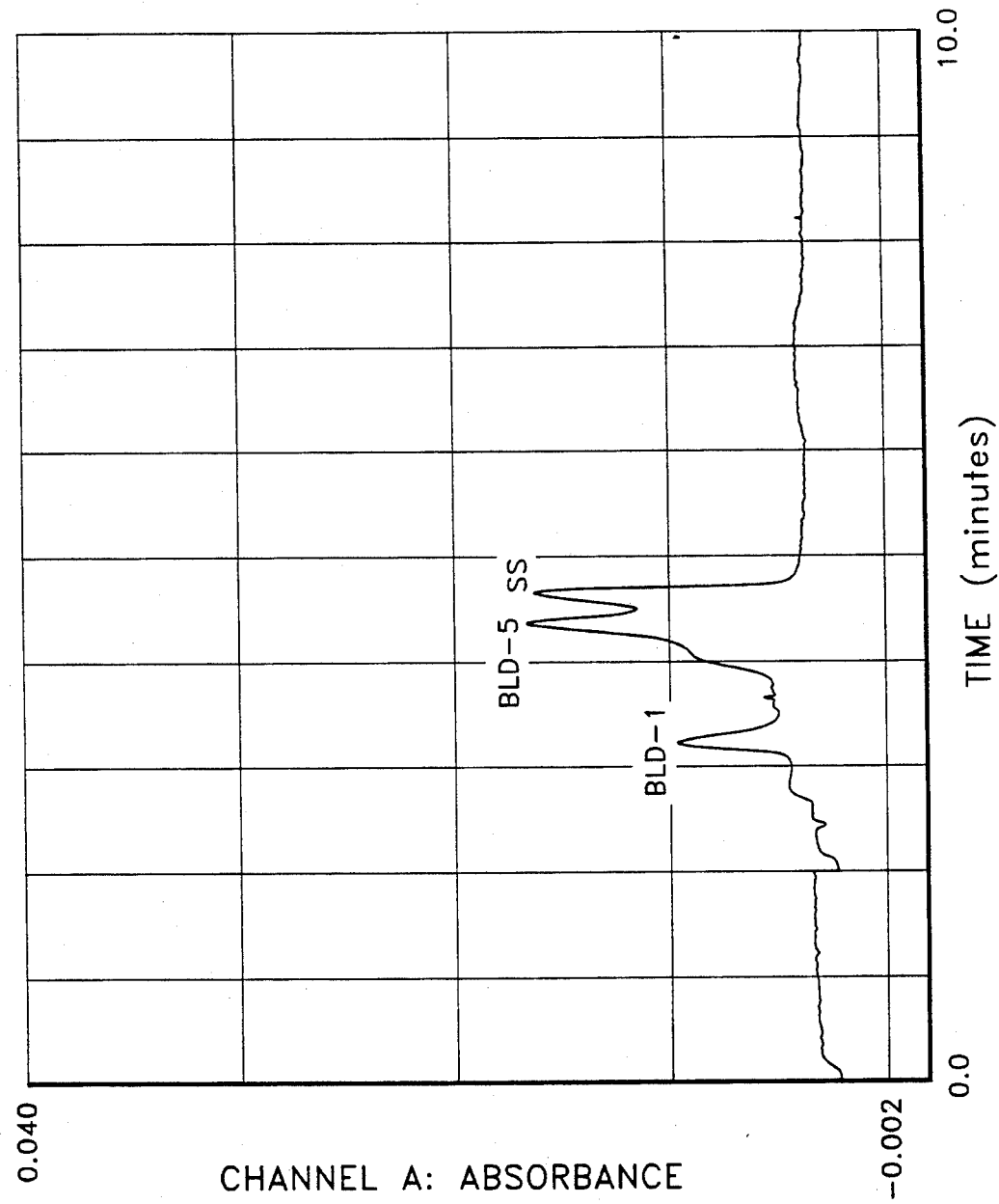
FIG. 4 is an electropherogram of the same materials of FIG. 2 with a park time of 90 seconds.

The electropherogram of FIG. 4 was achieved using a 90 second park period. In this electropherogram, the resolution is improved over that of FIG. 3, particularly between the BLD-5 and SS peaks. Accordingly, by following the predicted minimum park period for this system of 90 seconds, good resolution between the peaks was achieved.

Figure 5:
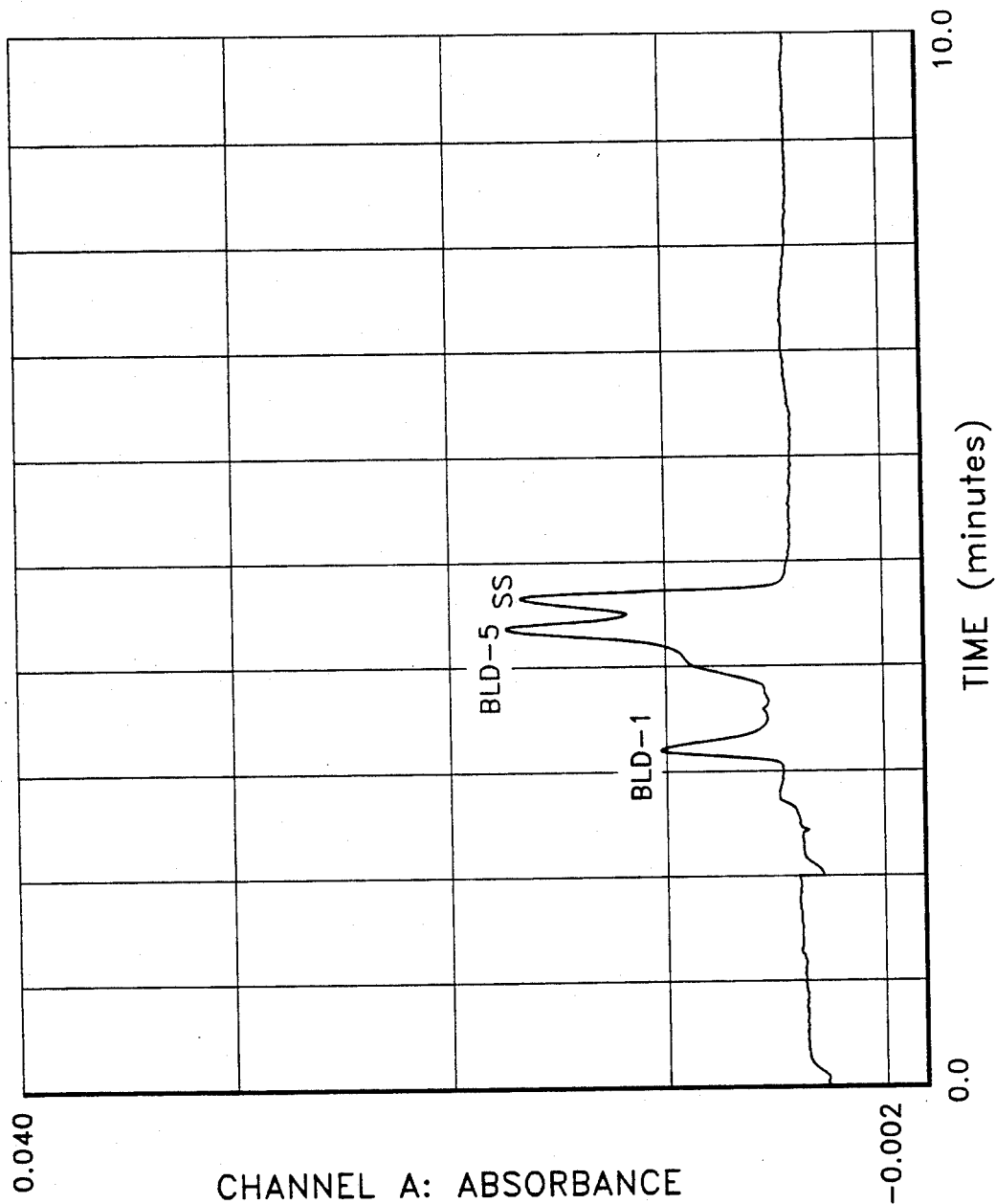
FIG. 5 is an electropherogram of the same materials of FIG. 2 with a park time of 180 seconds.

The electropherogram of FIG. 5 was achieved using a 180 second park period, twice that of the predicted minimum. Note that the resolution thereof is substantially similar to that of the resolution obtained in the electropherogram of FIG. 4. This too would be expected in that once a minimum park period is utilized for obtaining a desired absorbance peak, the amount of product produced does not dramatically affect the resolution.

The foregoing indicates that the park time minimum transformant of Equation 1 can be utilized to accurately determine a minimum park time necessary to achieve a sufficient signal for between-peak resolution and signal-to-noise ratio.

Example II-Procedure Validation

For Example II, the human LDH Isoenzyme Sample was utilized. For this example, about 0.003 Absorbance Units was desired. All other values were the same as in Example 1, except that U was 0.1 (one-tenth of the specified P→S value of 1.0). Accordingly, a predicted minimum park time is derived as follows:

$$t_{min} = \frac{\frac{0.003}{6300 \cdot 0.0075}}{.1 \cdot 10^{-6} \cdot 665.4 \cdot 1}$$

$$= .99 \text{ minutes} \approx 1.0 \text{ minute}$$

Note that if it was desirable to decrease this minimum park period, $T_1$ (running temperature) could be increased. For example, if $T_1$ was 37° C., then $t_{min}=0.67$ minutes.

As noted, $t_{min}$ is a minimum park period. Thus, it is possibl to increase this period of time, provided that substrate depletion does not occur. This can be prevented by utilizing at least twice the $K_m$ amount for the substrate. For these examples, approximately five times the value of $K_m$ was utilized, thus ensuring that the park time could be significantly increased without substrate depletion. Thus, the "limiting" factor on the park period, under these parameters, is primarily a function of the desired time for each analytical run. This time period can vary substantially, depending on the arena of analysis. In a clinical setting, this period can be dictated by the particular needs of the investigator. For Example II, the actual park period utilized was well in excess of the predicted minimum, i.e., about 10 minutes. The electropherogram results for the analysis are presented in FIGS. 6 and 7.

Figure 6:
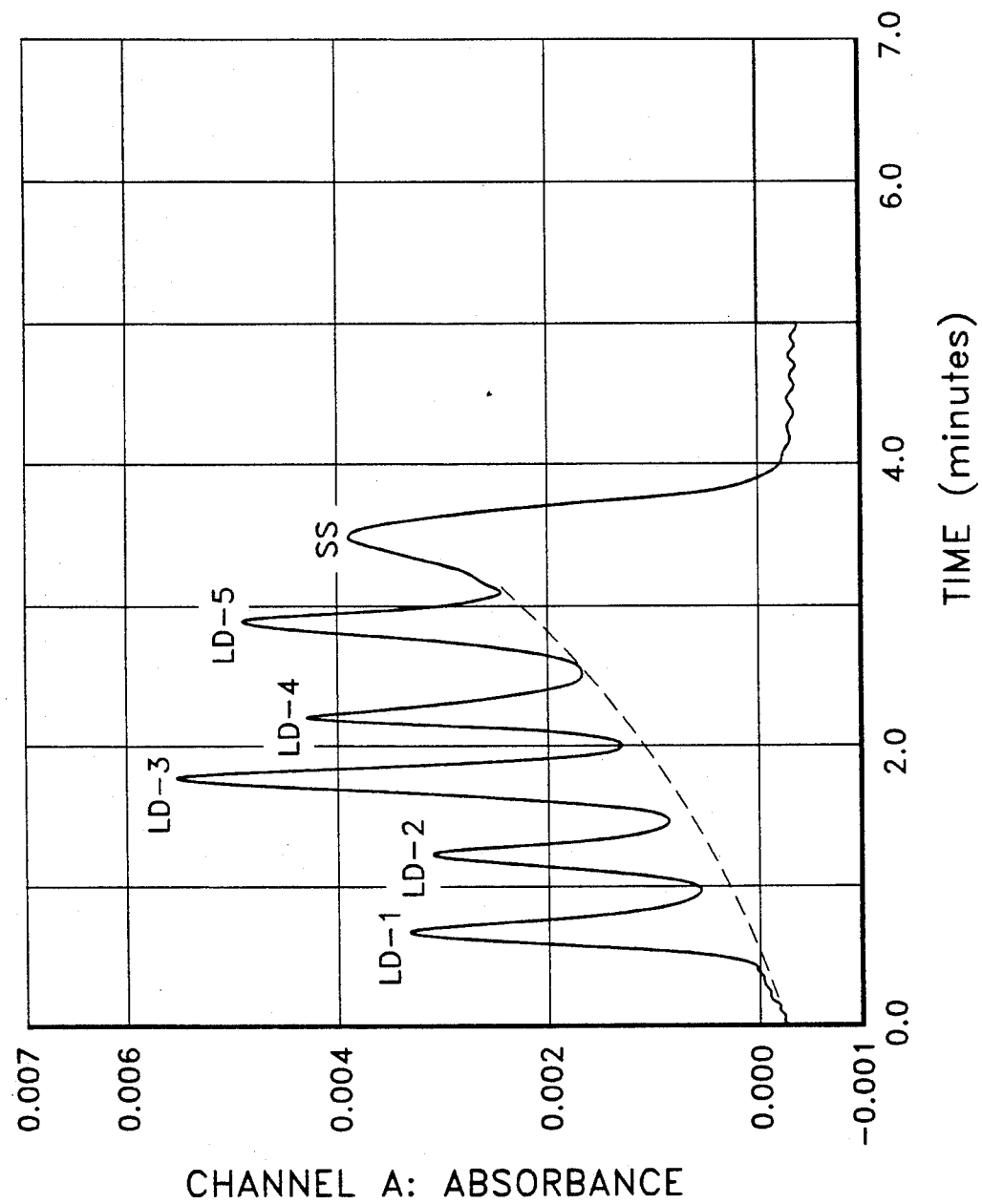
FIG. 6 is an electropherogram of five (5) peaks and a "sample shock" of NADH produced by the catalytic conversion of NAD+ and lactic acid by the five human LD isoenzymes.
Figure 7:
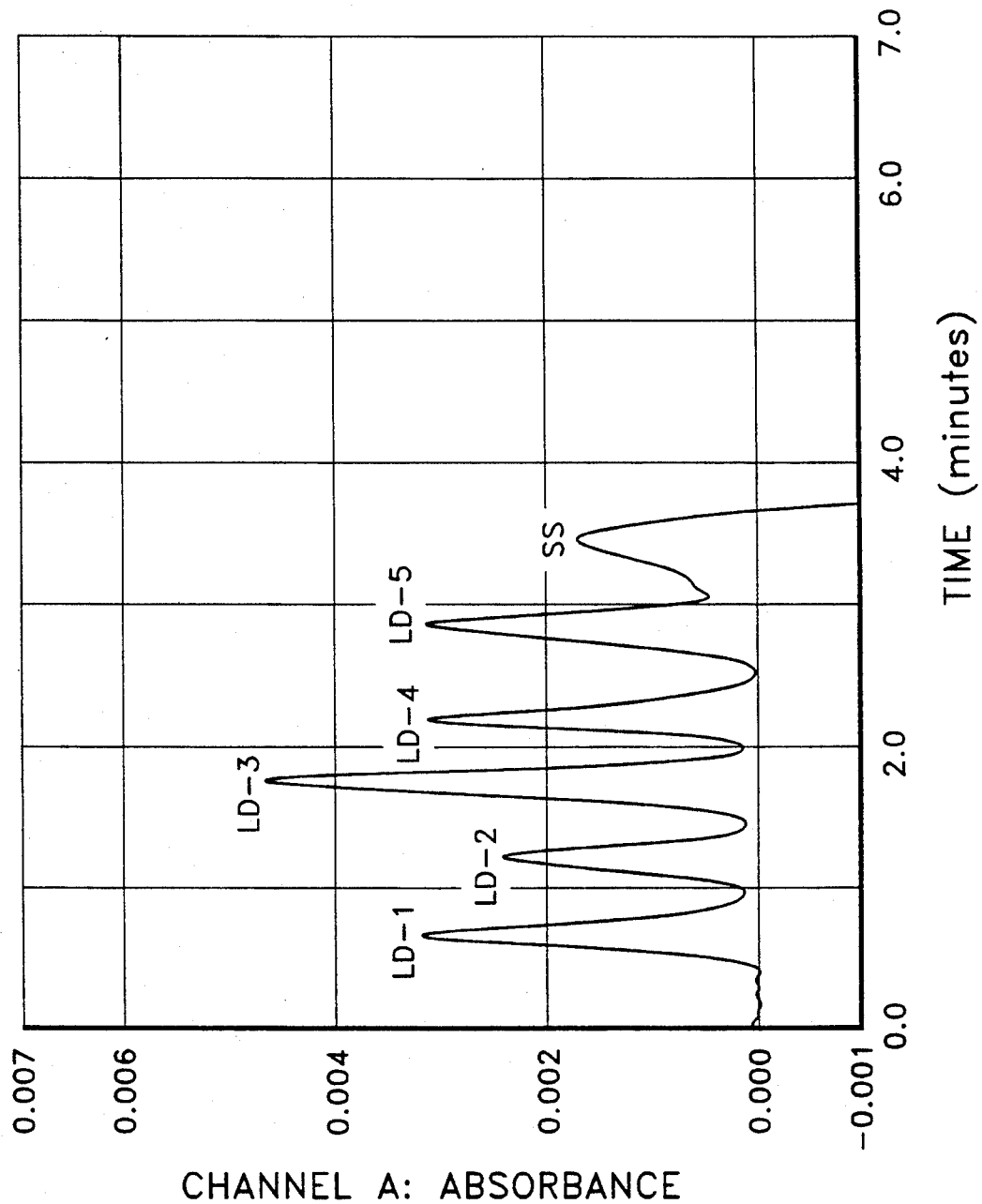
FIG. 7 is the electropherogram of FIG. 6, baseline-corrected.

As those in the art appreciate, CZE electrophoresis represent a "first-in-last-out" arrangement such that the first constituent to be detected, designated in FIGS. 6 and 7 as "LD-1", appears to be the last zone to be analyzed. The relevance of this is with respect to the "first" peak, designated as "SS" for "sample shock". As noted, immediately upon injection of the LDH Isoenzyme Sample into the Substrate buffer, the catalytic reaction begins, such that NADH is formed. This, of course, takes place irrespective of separation of the isoenzymes. As the substrate, enzymes and product proceed through the capillary, separation of the isoenzymes will begin such that defined "fronts" develop. Accordingly, the faster (relative) isoenzymes will react with substrate in regions different than slower isoenzymes. As demonstrated in Example I, without "parking" the sample, a continuum of product will form, defined by a generally small front caused by the faster isoenzymes through to generally larger front caused by the slower isoenzymes. This phenomenon is represented by the dashed line of FIG. 6 and comports with a consideration of the electrophoretic mobilities of isoenzymes as they simultaneously travel and catalyze the Substrate→Product reaction. As should be appreciated, merely advancing the isoenzyme-containing sample through the substrate buffer will not, in and of itself, evidence useful data relative to the isoenzyme relationships, as is shown by the dashed line portion of FIG. 6.

By "parking" the LDH Isoenzyme Sample-Substrate Buffer solution, however, the separated isoenzymes will principally catalyze the Substrate→Product reaction in the defined isoenzyme zones such that product, in this case NADH, is rapidly generated at the locus of each isoenzyme-separated fragment. Therefore, product is accumulated within these zones. Thus, when "parking" is discontinued, the concentrated product zones and the sample shock continuum continue through the capillary and are detected as a Sample Shock continuum including peaks which represent the effect of concentrated product production within the discrete zones. Accordingly, and as is shown in FIG. 6, it is possible to avoid the product-continuum via the methodology disclosed herein—good separation of the NADH product was achieved relative to each of the five LDH isoenzymes in the LDH Isoenzyme Sample.

For the LDH Isoenzyme Sample, following electro-kinetic injection, 7.5 kV was applied to the column for 2 minutes. This voltage and period of time is sufficient to separate the isoenzymes, although higher or lower voltages can be used in conjuction with shorter or longer, respectively, periods of time.

After the 2 minute separation period, the voltage was terminated, i.e., initiation of the "park" period began. Thus, the separated isoenzymes were, in essence, stationary within discrete zones. As noted, these zones are co-mingled with Substrate Buffer so that within each zone, product is generated based upon the catalytic reaction taking place within each zone. Following the park period, 7.5 kV was applied to the capillary such that the product moved from the stationary discrete zones to the detection window. Because the final "peak" (i.e., the sample shock) was detected within 4 minutes of injection, the total analytical time, including the park period, was about 14 minutes.

Another observation derived from FIG. 6 is that after the 10 minute park period, product diffusion is not a limitation under these parameters. This is of value because the park period utilized was ten times that of the minimum park period value derived.

The electropherogram of FIG. 7 was derived from the same data which led to the electropherogram of FIG. 6. In essence, the dashed-line portion of FIG. 6 has been subtracted from the Figure; this portion, as noted, is attributed to total sample shock over the course of the entire analytical run. Thus; by removing this portion from the electropherogram, FIG. 7 represents a baseline corrected analysis of the 5 LDH isoenzymes.

An alternative approach to the termination of the electric field to effectuate the park period is utilization of a "reverse pulse" protocol. Under such a protocol, the polarity of the CZE system is reversed, such that the discrete zones are pulled in a reverse direction back towards the area of sample injection. The reverse pulse protocol can be utilized in situations where it is desirable to utilize park periods in excess of about 60 minutes, or where product diffusion from the discrete zone may be a concentration. I.e., by simultaneously "pulling and pushing" the zones through the capillary, the zones do not remain in a discrete region during the product formation period. Methodologies for reversing the polarity of CZE systems are known to those skilled in the art and are not set forth in detail herein.

The foregoing data demonstrates that isoenzymes can be analyzed in a CZE format utilizing the methodology disclosed herein. It is to be understood that the foregoing Examples are not to be construed as limiting the invention. The disclosed methodology is applicable to isoenzyme systems other than those set forth in the Examples. Additionally, the methodology is not limited to the specified high performance capillary electrophoresis system utilized herein. Furthermore, the methodology is not to be construed as limited to analysis of clinical samples in that the methodology has broader applications to non-clinical samples comprises enzymes and/or isoenzymes. As such, the foregoing Detailed Description and Examples are not intended, nor are they to be construed, as a limitation on the disclosed methodology or the claims to follow. Modifications and equivalents which are within the purview of the skilled artisan are considered to be included within the scope of the invention as claimed.

What is claimed is:

1. A capillary zone electrophoresis method for the determination of isoenzyme constituents comprising the steps of:
   a) introducing an isoenzyme-containing sample and substrate which is capable of being catalyzed by said isoenzymes into a reaction product into a capillary tube including therein a buffer;
   b) subjecting said sample to capillary zone electrophoresis techniques by applying an electric field to said capillary tube of sufficient voltage to allow for separation of said isoenzymes into discrete zones within said capillary tube;
   c) terminating the application of said electric field;
   d) allowing a sufficient period of time to transpire for said isoenzymes to catalytically convert said substrate to said reaction product within said discrete zones;
   e) moving said reaction product through said capillary tube to a product detection region; and
   f) detecting said product wherein the distribution of said detected product is determinative of said isoenzyme constituents in said sample.

2. The method of claim 1 wherein said sample is introduced into said capillary tube by a protocol selected from the group consisting of electrokinetic injection and pressure injection.

3. The method of claim 1 wherein said product is moved to said product detection region by a protocol selected from the group consisting of application of an electric field to said capillary of sufficient voltage to move said product, and application of external pressure to said sample of sufficient force to move said product.

4. The method of claim 1 wherein said substrate has a defined $K_m$ value.

5. The method of claim 4 wherein the amount of said substrate in said buffer is at least about two times the value of $K_m$.

6. The method of claim 1 wherein said detection is achieved by irradiating said product and obtaining an absorbance value therefore.

7. The method of claim 6 wherein a minimum period of time for terminating said electric field is determined by
   a) obtaining a numerator value, the numerator value being obtained by dividing a desired absorbance value for said product by a first value, the first value being obtained by multiplying the molar extinction coefficient of said product by the value of the length of a measurement of said irradiation through said capillary;
   b) obtaining a denominator value, the denominator value being obtained by multiplying a unit activity value for said enzyme by the molecular weight of the product, the value $10^{-6}$, and a quotient value, the quotient value being obtained by dividing the running temperature of the capillary electrophoresis system by the enzyme calibration temperature; and
   c) dividing the numerator value by the denominator value.

8. The method of claim 7 wherein said length of said irradiation measurement is the internal diameter of said capillary tube.

9. The method of claim 1 wherein said sample is a clinical sample.

10. A capillary zone electrophoresis method for the determination of clinical isoenzyme constituents comprising the steps of:
    a) introducing a clinical sample and a substrate capable of being catalyzed by clinical isoenzymes into reaction product into a capillary tube including therein a buffer;
    b) subjecting said sample to capillary zone electrophoresis techniques by applying an electric field to said capillary tube of sufficient voltage to allow for separation of isoenzymes within said sample into discrete zones within said capillary tube;
    c) terminating the application of said electric field for at least a minimum time period, said minimum time period determined by:
       1) obtaining a numerator value, the numerator value being obtained by dividing the desired absorbance value for said product by a first value, the first value being obtained by multiplying the molar extinction coefficient of said product by the value of the internal diameter of said capillary;
       2) obtaining a denominator value, the denominator value being obtained by multiplying the unit activity value for said enzyme by the molecular weight of the product, the value $10^{-6}$, and a quotient value, the quotient value being obtained by dividing the running temperature of the capillary electrophoresis system by the enzyme calibration temperature; and
       3) dividing the numerator value by the denominator value to obtain said minimum time period;
    d) moving said reaction product through said capillary tube to a product detection region by applying an electrical field to said capillary tube of sufficient voltage to allow for movement of said product; and
    e) detecting said reaction product wherein the distribution of said detected product is determining of said enzyme constituents in said sample.

* * * * *